United States Patent [19]

Hirsch et al.

[11] Patent Number: 5,292,773

[45] Date of Patent: Mar. 8, 1994

[54] TREATING AIDS AND HIV INFECTION WITH METHIONINE

[76] Inventors: Gerald P. Hirsch, 3136 Brook Dr., Decatur, Ga. 30033-3912; Robert K. Bayless, 6402 Woodhue Dr., Austin, Tex. 78745-3836

[21] Appl. No.: 845,157

[22] Filed: Mar. 2, 1992

Related U.S. Application Data

[63] Continuation-in-part of Ser. No. 479,961, Feb. 14, 1990, abandoned.

[51] Int. Cl.$^5$ ............... A01N 37/30; A01N 37/12; A01N 37/44; A61K 31/13
[52] U.S. Cl. ................... 514/554; 514/561; 514/562; 514/579
[58] Field of Search ............... 514/554, 561, 562, 579, 514/706

[56] References Cited

U.S. PATENT DOCUMENTS

| | | | |
|---|---|---|---|
| 3,952,115 | 4/1976 | Damico et al. | 426/615 |
| 4,315,028 | 2/1982 | Scheinberg | 424/290 |
| 4,711,780 | 12/1987 | Fahim | 514/562 |
| 4,902,871 | 2/1990 | Bayless et al. | 514/562 |
| 4,927,850 | 5/1990 | Bayless et al. | 514/562 |
| 5,053,429 | 10/1991 | Hirsch et al. | 514/562 |
| 5,084,482 | 1/1992 | Hirsch et al. | 514/562 |

FOREIGN PATENT DOCUMENTS

| | | |
|---|---|---|
| 9109524 | 7/1991 | European Pat. Off. . |
| 0519876 | 12/1992 | European Pat. Off. . |
| 2821704 | 11/1978 | Fed. Rep. of Germany . |
| 3707127 | 9/1988 | Fed. Rep. of Germany . |
| 9112809 | 9/1991 | PCT Int'l Appl. . |

*Primary Examiner*—Nathan M. Nutter

[57] ABSTRACT

This invention concerns novel safe compositions containing as an active antioxidant or antiinflammatory agent and thiol-repleting agent, the amino acid methionine, and/or one or more related compounds including certain metabolic precursor compounds, and novel methods employing the compositions for treating or amelio-rating symptoms of human immunodeficiency virus infection and AIDS, such as weight loss, increased red cell sedimentation, and leukoplakia; novel methods employing the compositions for treating or inhibiting symptoms resulting from nutritional deficiencies of methionine; and novel methods employing the compositions for inhibiting or preventing triglyceride elevation due to low dose methionine consumption. The compounds include the methionine hydroxy analogs, as well as compounds having the structural formula $$CH_3S(CH_2)_2-\underset{\underset{NH_2}{|}}{CH}-COOH$$

1-, dl- or d- form and pharmaceutically acceptable N-(mono- and di-carboxylic acid) acyl derivatives and alkyl esters thereof.

1 Claim, No Drawings

TREATING AIDS AND HIV INFECTION WITH METHIONINE

CROSS-REFERENCES TO RELATED APPLICATIONS

This application is a continuation-in-part of application Ser. No. 07/479,961, filed Feb. 14, 1990 and now abandoned.

BACKGROUND OF THE INVENTION

1. Field of the invention

This invention concerns improved antiinflammatory compositions containing the amino acid methionine (also known as "Met"), and/or one or more related compounds including certain metabolic precursor compounds with the amino acids glycine and serine to reduce side effects of methionine at low doses and novel methods employing the compositions for treating inflammatory AIDS symptoms and HIV infection in man. Compositions are suitable for the treatment of disease conditions of man that may be attributable to or result from nutritional deficiency or illness resulting from uncontrolled inflammatory responses.

2. Description of the Related Art

A variety of efforts have been made over many years to elucidate the mechanisms and origins of inflammation and the various forms of disease it may cause and to identify disease conditions which involve inflammatory damage. Limited success has been achieved in identifying such conditions in alleviating the symptoms of diseases having inflammatory components. Oxidative stress has been implicated in many of these diseases, and antioxidant therapy has been recommended as one method to alleviate the damage it causes (Cross, et. al., Annals of Internal Medicine, 107:526–45, 1987). Successful prevention of oxidative stress damage requires that normal physiological parameters and functions be maintained so that undesired side effects do not occur.

It is now generally accepted that an essential component for the occurrence of the disease known as AIDS (Acquired Immunodeficiency Syndrome) is an infection by a virus now designated Human Immunodeficiency Virus (HIV). This virus can be transmitted by the exchange of body fluids, including unprotected sexual intercourse, blood transfusions, and through sharing of non-sterile hypodermic needles. Blood borne occupational exposure is also known.

What has puzzled doctors and researchers in trying to understand the disease of AIDS is the aspect of latency. Latency is the term used to describe the long time period between a cause and its effect. With regard to the progression of the AIDS disease from an early symptomless stage of infection which can be demonstrated by the production of antibodies to the virus to the eventual occurrence of symptoms typical of the disease state, such as recurrent infections, weight loss, Karposi's sarcoma, etc., the period of latency can be longer than 7 years. In one study (Arendrup, et al., Scand. J. Infect. Dis. 21:19–26, 1989) 5 of 10 persons with HIV antibodies remained healthy over a 5 year period. In most disease conditions the symptoms of the infection occur immediately or soon after the infection. The progression from the state of being healthy but showing evidence of infection with HIV to becoming sick with AIDS symptoms is associated with decrease in the number of T-helper cells designated CD4, a decrease in the body's production of antibody to the viral antigen p24, and increase in HIV antigen in the blood (Bottiger, et al., Scand J. Infect. Dis. 21:507–14,1989).

Because of the long latency that particular individuals show after HIV infection it seems clear that other factors in addition the virus itself contribute to the occurrence of the disease symptoms. By understanding the important elements operating that may allow infected individuals to delay the deleterious effects of the virus infection, considerable health benefits can be achieved for the antibody-positive, HIV infected person.

A benefit of compounds which modulate the activity of the immune system of HIV-infected people is based on the hypothesis that the initial stages of the disease result in generalized immune system activation. Over time, this generalized stimulation results in activated immune cells which do not respond to further stimulation. The hypothesis includes the concept of immune system failure after an extended period of hyper-activity (Ascher and Sheppard, J. Acquired Immune Deficiency Syndromes, 3:177–91, 1990). The authors postulate that one possible mode of therapy is ". . . to target specific mediators that produce fever, cachexia, and diarrhea, and inhibit their action."

Recent identification of homology between the HIV viral protein designated "Nef" and a region of the histocompatibility antigens of HLA II, lends support to the hypothesis of an important involvement of autoimmunity in leading to eventual HIV immunosuppression (Vega, M. A., Guigo, R., and Smith, T. R., Nature 345: 26 (1990). The underlying theory is that the "Nef" protein region serves as a false signal to the immune system mimicking that signal responsible for the stimulation which results when the histocompatibility antigen sites of immunoglobulins stimulate these cells as antigen-antibody complexes.

Severe liver damage occurs after consumption of large doses of acetaminophen. Acetaminophen is converted by a cytochrome P-450 oxidase to a reactive metabolism that is then inactivated by conjugation with glutathione. When large doses of acetaminophen are consumed, hepatic glutathione stores are depleted, and excess reactive metabolites cause cell damage (Vale, et.al., Arch. Internal Med., 141:394–6, 1981). Thus, acetaminophen poisoning is a good model to study the effects of thiol depletion. N-acetylcysteine (NAC) and l-methionine are the currently used antidotes for acetaminophen overdoses. Intravenous administration of NAC can cause anaphylactoid reactions, and large oral doses of methionine can cause nausea and vomiting (Neuvonen, et al., Internat. Jour. Clinical Pharmacology, Therapy and Toxicology, 23:497–500, 1985). The addition of selenium and serine to the methionine and vitamin B6 dosage allows the hepatic cells to maximize the production of intracellular glutathione and extracellular glutathione peroxidase (Luo, et. al., Am.J. Clin. Nutrition, 42:4–48, 1985, and Sunde and Evenson, J. Biol. Chemistry, 262:933–7, 1987). The ability to maximize glutathione and glutathione peroxidase production, while having an immediate antioxidant benefit and glutathione-sparing effect may be of value in other disease states where reduction of glutathione levels may be a toxic mechanism. Reduced glutathione effects include:

1) ataxia-telangiectasis (Meredith and Dodson, Cancer Research, 47:4576–81, 1987);
2) human immunodeficiency virus infection (HIV) where blood levels of glutathione are reduced in HIV positive persons (Buhl, et. al., The Lancet, Vol. 1 No. 8675, p. 1294-8, 1989);

3) rheumatoid arthritis (Braven et al., Br. J. Rheumatology, 28;212-15, 1989; and Banford, et al., Rheumatology Internat 2:107-11, 1982);

4) Parkinson's Disease (Riederer, et. al., Jour. of Neurochemistry, 52:515-20, 1989).

dl-Methionine is a chemically manufactured source of the essential amino acid l-methionine which contains an equal amount of the mirror image d-methionine analog. The d-analog is not converted to the natural l-methionine by humans (although it can be utilized by animals such as dogs, chickens, etc.) and thus does not have nutritional value for protein production. l-Methionine is converted in the body tissues to the amino acid cysteine, the other sulfur amino acid present in most proteins, by enzymatic reaction with another amino acid serine. Multiple benefits of dl-methionine when taken with the amino acid serine, or the amino acid glycine, which is converted to serine in the body, are thought to arise from both the metabolic and anti-oxidant properties of dl-methionine. The metabolic properties of l-methionine include:

1. Providing methyl groups for many methylation reactions.
2. Providing homocysteine for the transulfuration pathway through cystathionine for the production of the amino acid cysteine, which is present in high concentrations in hair.
3. Through cysteine production it provides glutathione, a three amino acid compound which acts as an antioxidant in cells and in the blood.
4. Through cysteine production and the conversion of cysteine by the body to hypotaurine, another antioxidant which is normally present in the seminal fluid.
5. Through hypotaurine production and conversion in the body it provides taurine, another antioxidant amino acid, which is the highest in concentration of all the free amino acids in cells. It is especially high in concentration in nerve cells and some white cells.

Additional serum antioxidant properties are provided by the use of d-methionine which is due to the ability of d-methionine to provide sustained elevated blood levels of methionine. This occurs because d-methionine is poorly metabolized. However, d-methionine is equally as effective as l-methionine as an anti oxidant. (Stegink, et al., Jour. Nutrition, 116:1185-92, 1986) and (Tsan and Chen, J. Clinical Investigation 65:1041-50, 1980).

The amino acid glycine may be included when seeking optimal benefits of the antioxidant methionine metabolites such as cysteine, glutathione, hypotaurine and taurine because when normal subjects are given 9 grams of l-methionine per day on an adequate diet, urinary glycine excretion levels are reduced. No other urinary amino acid was altered (Block, et al., J. Nutrition, 86:256-64, 1965).

Consumption of oral methionine at 8 grams daily caused a 30% reduction in serum folate levels in five healthy subjects (Connor, et al., Postgraduate Medical Jour., 54:318-20, 1978).

Excess methionine causes the urine to become acid and in so doing stimulates the excretion of calcium (Tschope, Mineral Electrolyte Metab. 11:137-9, 1985). Calcium supplementation of about 20 milligrams per gram of methionine consumed would compensate this additional loss.

HIV-positive persons have benefitted from antioxidants. Studies with compounds that act as water-soluble antioxidants often have serious side-effects.

A recent study of 13 asymptomatic HIV infected patients treated with oral D-penicillamine demonstrated complete inhibition of virus expression in 60% of those treated (Schulof, et al., Arzneim.-Forsch. Drug Res. 86 (II), No. 10, 1986). The basis for the human experiment was a previous cell culture test which showed the D-penicillamine totally inhibited viral growth at 40 microgram/ml, less that 10% of the cellular toxic dose. Of 10 patients completing at least 2 weeks of treatment, 3 tested negative for HIV six weeks after cessation of treatment by measurement of reverse transcriptase, antigen p15 and antigen p24. Side effects of the treatment protocol were significant with 4 of the 13 patients developing skin rashes and 2 developing mild elevations of hepatocellular enzymes (SGOT, SGPT) indicative of liver damage.

The rationale for testing D-penicillamine in HIV infection was based on its ability to interact with proteins and peptides by the formation of mixed disulfides and thus inactivate cysteine-rich essential viral proteins, a high concentration of which are found in HIV.

D-penicillamine is used to treat rheumatoid arthritis where its benefit is thought to arise by reducing the damage done by the oxidative products released during inflammation (Munthe. et al., In: Modulation of Autoimmunity and Disease, Maini and Berry, Eds., Praeger, London, 1981, p. 134-42) and (Cross, et al., Annals of Internal Medicine, 107:526-45, 1987). Of particular concern are the polymorphonuclear neutrophils (PMNs). These cells release relatively large amounts of oxidizers and proteolytic enzymes when activated (Weiss, New Eng. J. Medicine, 320:365-76, 1989). They can cause wide-spread tissue damage, with oxygen metabolites being identified as the most destructive toxins. Thus, in active disease states due to infection, highly reactive free radicals can be expected to be released by immune cells, including the PMN and the macrophage.

The benefit of reducing compounds in the treatment of AIDS was shown in a double-blind clinical trial using diethyl-dithiocarbamate (DTC) as a reducing agent. The treatment of HIV-positive persons once a week for a 4 month period showed in the treatment group (1) fewer persons progressing to AIDS, (2) a high percentage showing disappearance of diarrhea, weight loss or persistent fever, and (3) disappearance of splenomegaly. No change was detected in virus blood levels as measured by reverse transcriptase activity (Lang, et. al., Lancet, Sep. 24, 1988, p. 702-6). In another study this same compound slowed the progression of the disease during the 6-month trial period (Reisinger, et. al., Lancet, 335:679-82, 1990). DTC is known to interfere with glutathione metabolism, while substituting for it as an anti-oxidant. When the AIDS patients were removed from DTC, clinical benefits were progressively lost.

In a separate study using DTC, which was administered by injection rather than orally, there was significant improvement in symptoms and in reduction of lymphatic disease (Brewton, et al., Life Sciences 45: 2509-2520, 1989). Benefits of DTC may be due to reduction of fungal infections (Allerberger, F., et al., Mycoses 32: 527-530, 1989).

Free radical reducing compounds may benefit HIV patients as a result of the maintenance of blood and tissue glutathione levels. Glutathione serves as an intracellular reducing agent and antioxidant (Deneke, et al.,.

Am. J. Physiology, 257:163-73, 1989). Buhl, et al. (Lancet, Vol. 2 No. 8675, Dec. 2, 1989) showed that symptom-free HIV positive individuals have only about half the level of plasma glutathione as compared to healthy controls. A majority of HIV-positive patients tested, had abnormally low glutathione levels in lung epithelial lining fluid. Dworkin, et. al. (Biological Trace Element Research 15:167-77, 1988) showed that glutathione peroxidase, which is an extracellular antioxidant, was 47% less in 13 AIDS patients, compared to 14 healthy controls. Plasma selenium was also similarly reduced in AIDS patients.

In animal cell studies methionine is equally as effective as cysteine as a precursor for glutathione biosynthesis (Reed and Orrenius, Biochem, Hiophys, Res, Comm. 77: 1257-64, 1977). Rat feeding studies show that methionine can raise liver and muscle glutathione levels (Seligson and Rotruck, J. Nutrition 113:98-104, 1983). In humans, the plasma half-life of a 100 mg i.v. dose of glutathione is 1.6 minutes (Wendel and Cikryt, FEBS Letters, 120: 209-11, 1980).

Kalebic, et al., (Proc Natl. Acad. Sci. USA, 88:986-90, 1991) show that glutathione, glutathione ester, and N-acetylcysteine, at a dose of 15 mM, were able to suppress HIV protein synthesis in vitro. The authors speculate that ". . . these or similar agents may have therapeutic value in HIV-infected patients."

One mediator produced by the activated macrophage is a hormone called "cachectin" or "tumor necrosis factor". This hormone produces anorexia and profound wasting then injected chronically into mice (Beutler, B., Nutrition Reviews, 46: 369-73, 1988). It also causes the PMN (polymorphonuclear neutrophil white cell) to degranulate, release its granule contents, and activate the respiratory burst which releases oxidative radicals (Balkwill, F. R., British Medical Bulletin, Vol. 45 No. 2, p. 389-400, 1989 and Larrick, et al., Blood, 69:640-4, 1987). AIDS patients have been shown to have increased serum values of cachectin/Tumor necrosis factor (Lahdevirta, et al.. Am. J. of Medicine, 85:298-91, 1988). AIDS patients also show elevated levels of circulating triglycerides (Grunfeld, et al., Am. J. of Medicine 86:27--, 1989) which may be an effect of cachectin which has been shown to inhibit lipoprotein lipase (Fried and Zechner, J. of Lipid Research, 30:1917-23, 1989).

Tumor necrosis factor stimulates the production of HIV virus in MOLT-4 cells while another neutrophil (PMN) activator, phorbol 12-myristate 13-acetate, stimulates HIV virus replication in human peripheral blood mononuclear cells. N-acetyl cysteine, (NAC) an antioxidant utilized to counteract oxidative stress such as that which occurs with acetaminophen overdose, and which also increases intracellular glutathione, has been tested for its effect on virus replication in MOLT-4 cells and mononuclear cells (Roederer, M., et al., Proc. Natl. Acad. Sci. USA 87: 4884-4888, 1990). NAC at 3 mM reduces virus production in MOLT-4 cells by more than half, but more than 10 mM is required to reduce virus production by this amount when the virus production is stimulated by tumor necrosis factor. In human mononuclear cells, NAC reduces phorbol-induced virus production by more than half at 1 mM. More than 3 mM NAO is required to reduce virus production in infected, unstimulated mononuclear cells. Doses of NAC required to achieve blood or tissues level above 3 mM are much higher than those achieved by previously approved uses of NAC.

PMNs have also been demonstrated to predominate in the cerebrospinal fluid (OSF) of AIDS patients who have cytomegalovirus infection in the nervous system (de Gans, J., et al., J. of AIDS, 3:1155-8, 1990).

Anemia is another complication of AIDS. Anemia of chronic disease is commonly seen, and may be due to inflammatory mediators released by macrophages. Controlling inflammation in AIDS may allow blood values to normalize (Baer, et al., Seminars in Arthritis and Rheumatism, 19 (4): 209-23, 1990).

A recent study in mice showed that infection with influenza virus led to a forty-fold increase in an enzyme called xanthine oxidase. This enzyme causes a generalized oxidative reaction in tissue. Administration of superoxide dismutase, a free radical scavenger, could prevent death in mice which would otherwise occur. Virus titers dropped by day four, while xanthine oxidase conversion peaked on day eight, when death occurred, unless SOD was intravenously administered. The implication of these studies is that the oxidative attack generated by xanthine oxidase was the direct cause of death, not the virus (Oda, et. al., Science, 244:974-6, 1989). Xanthine oxidase is produced in tissues by the oxidation of exposed sulfhydryls in xanthine dehydrogenase. This oxidation can be accomplished by oxygen introduced during reperfusion, or presumably by oxidative products of PMN (Parks and Granger, Acta Physiol. Scand. Suppl. 548:87-99, 1986). Another study, using the hamster cheek pouch method, shows that methionine was able to completely inhibit the vascular changes which xanthine oxidase would otherwise induce (Del Maestro, et al., In: Biological and Clinical Aspects of Superoxide and Superoxide Dismutase, No. 62, Bannister and Bannister, Eds., New York, 1978, p. 127-40). This inhibition was believed to be due to the known hydroxyl radical scavenging effect of methionine. Methionine has been shown to inhibit both PMN oxidative products as well as xanthine oxidase free radical production. It has been hypothesized that the damage seen in AIDS is oxidative in nature, and that the use of appropriate antioxidants is warranted (Papadopulos-Eleopulos, E., Medical Hypotheses 25:151-62, 1988).

In addition to its potential antioxidant benefits, dl-methionine provides 1-methionine for supplemental nutrition. Methionine and cystine blood levels are reduced 25% in AIDS patients (Droge, et al., Biol. Chem. Hoppe-Seyler 369:143-8, 1988), which further reduces the body's ability to produce glutathione (see above). This reduction is significant in light of the fact that plasma methionine levels were not reduced in eight healthy subjects after seven days of starvation (Martensson, J., Metabolism 85:118-21, 1986).

Another problem found in pediatric AIDS is a large reduction of folic acid (80% of normal) in cerebral spinal fluid (OSF), which may cause the demyelination of nerve fibers seen in AIDS. Accompanying the folate reduction was a 50% reduction of CSF S-adenosylmethionine, the principal methyl donor in the brain (Surtees, et al., The Lancet, 335:619-21, 1990).

Folate deficiency has also been reported in HIV infected adults at various degrees of progression of the disease. Simple folate supplementation corrected this deficiency (Boudes, P., Zittoun, J., and Sobel, A., Lancet 335: 1401-1402, 1990).

The pharmacopeia advises that methionine should not be taken by persons with active kidney or liver disease. Persons on chemotherapy taking folate inhibitors such as methotrexate or trimetrexate should not take methionine or folate.

Methionine is not recommended for persons being treated with monoamine oxidase inhibitors such as deprenyl. Schizophrenic patients given 300 mg per kg of l-methionine per day exhibited symptoms of intoxication (The Martindale Pharmacopoeia, 26th Ed., The Pharmaceutical Press, London, p 76, 1972)

Methionine deficiency is not recognized as a disease state in modern countries where adequate total protein is generally available. While it is recognized that humans, in contrast to most other mammals, cannot utilize d-methionine as a source of methionine, it is generally assumed that humans can utilized methionine sulfoxide as a source of methionine. The only suggestion that methionine sulfoxide might not be nutritionally equivalent to methionine is the lack of increase of blood l-methionine after administration of l-methionine sulfoxide. Human enzymes have been found that can reduce methionine sulfoxide to methionine.

Methionine is known to be affected by a variety of food processing activities. l-Methionine is converted to d-Methionine when proteins are heated and a significant amount of the nutritional value of methionine can be lost by this mechanism. However, most of the potential loss of available methionine occurs through the mechanism of oxidation of methionine to methionine sulfoxide. The bleaching of flour may be the major cause, when during the process of bleaching the chlorine is able to react with methionine. When proteins are heated with reducing sugars methionine is readily oxidized so that items such as fruit "canned" in natural sugars are potential sources of food source with a deficiency of available methionine. More recently, as unsaturated fats replace saturated fats in prepared food sources, additional cases of methionine oxidation occur. For example, the unsaturated fats in cake-mixes held in a hot warehouse would result in oxidation of methionine to its sulfoxide. Published evidence for an extensive loss of methionine in food processing as regards human nutrition occurred in the manufacture of instant oatmeal where the product used in nitrogen balance studies apparently had no nutritionally available methionine (see Kies, et. al., J. Nutrition, 105:809-4, 1975). In the cooking of several types of beans 40% to 50% of the methionine is not available to rats (Sawar and Peace, J. Nutrition. 116:1172-84, 1986). The dietary requirement for methionine plus cysteine is based on nitrogen balance studies where a total of 800 mg per day is required to bring 50% of adults into positive nitrogen balance. No attempt has been made to determine the level of methionine that might be optimal for the prevention of oxidative damage.

Methionine has been shown to be a target for the products of stimulated polymorphonuclear neutrophils (Tsan and Ohen, J. Olin. Invest., 65:1041-50, 1980). The granular fraction of the PMNs oxidizes methionine to its sulfoxide in the presence of peroxide. Peroxide does not oxidize methionine to its sulfoxide at normal physiological concentrations.

Some of the differences measured in the relative effectiveness of methionine compounds and other chemicals, especially sulfhydryl reducing substances, may be attributed to the control mechanisms that operate in animals and man to regulate the amounts of these substances, where giving more of a substance does not significantly increase blood and tissue levels of that substance. Stegink, (Jour. Nutrition,116:1185-92, 1986), showed that 0.5 gm of methionine elevated total blood methionine 2-fold for 2 hours with l-methionine but 3-fold for 4 hours with d-methionine. In the same study it was shown that methionine sulfoxide administration did not result in elevation of blood methionine. This observation suggests that methionine sulfoxide is not readily reduced to methionine but it is possible that this reduction occurs in tissues where the methionine remains sequestered. l-Methionine is an essential amino acid for human nutrition. The normal serum level of methionine in man is 15 ppm. dl-Methionine is available as a one-a-day food supplement in 500 mg. oral tablet form.

Regarding human nutrition, l-methionine is an essential amino acid whereas d-methionine is non-nutritive. For purposes of metabolism, l-methionine via S-adenosylmethionine has an important methylating function. In this function it loses a methyl group from its sulfur atom to become homocysteine. Homocysteine in excess can lead to homocysteinuria, and may be heart disease associated (Malinow, et al., Circulation 79:1180-88, 1989 and Olszewski and Szostak, Atherosclerosis 69:109-13, 1988). Folic acid has been shown to be an innocuous method to reduce plasma homocysteine levels (Brattstrom et al., Scand. J. Clin. Lab. Invest. 48:215-221, 1988). Administration of 8 grams of l-methionine to adult subjects for four days caused a greater than 30% reduction in serum folate levels (Conner, et al., PostGrad. Med. J. 54:318-20, 1978).

Administration of large amounts (5 to 10 grams per day) of l-methionine can cause gastrointestinal upset. Many people report a burning sensation in the stomach after taking methionine, along with an upset stomach and flatulence (Delrieu, et al, Revue du Rhumatisme, 55:995-7, 1988) Enteric coating and timed-release formulations should avoid the stomach problems and allow even elevations of blood methionine for maximum antioxidant effect. Typical enteric coating agents include cellulose acetate phthalate, and other cellulose ethers and derivatives (Johnson, J. C., in Sustained Release Medications, Noyes Data Corp, N. J., 1980, p.14).

The Food and Nutrition Board of the U.S. National Academy of Sciences has established the Recommended Daily Allowance (RDA) for nutrients for most healthy individuals. For a discussion, see The Nurses Guide to Drug Therapy, Eisenhauer and Gerald, Prentice-Hall, New Jersey, 1984-5, pages 84–602). RDA's include: Vitamin A: 5000 I.U.; Vitamin B12:3 mcg.; Vitamin B6: 2 mg; Vitamin B3: 18 mg ; Folic Acid: 400 mcg.; Vitamin C: 100 mg ; Vitamin D: 400 I.U ; Vitamin E: 15 I.U : Calcium: 800–1200 mg.; Iron: 18 mg.: Selenium: No RDA has been established, but the maximum non-toxic suggested dose is 200 mcg. per day; zinc: 15 mg. For a review of lifestyle risk factors and of protective factors in the diet, see the article by Bruce N. Ames entitled "Dietary Carcinogens and Anticarcinogens", Science, 221:256-68, 1983.

Epidemiological evidence in man correlates elevated blood level of triglycerides with increased occurrence of gallstones. Also, low serum cholesterol levels are associated with a high prevalence of gallstone disease. Thus, dietary methods to lower serum cholesterol may increase the risk of gallstones if serum triglyceride levels are not lowered at the same time. (Angelico, et al., In: Epidemiology and Prevention of Gallstone Disease, Capocaccia, L., et al, eds. MTP Press Ltd., Boston, 1984, p. 77-84). Yanagita et al., (Agricultural and Biological Chemistry, 48:815-6, 1984) show that administration of methionine to rats causes a doubling of hepatic triglycerides. However, Sugiyama, et al , (Agric. Biol. Chem., 49:3455–61, 1985) showed that the addition of glycine to a methionine supplemented diet had no effect on the elevation of triglycerides caused by the methionine.

The patent to Scheinberg U.S. Pat. No. 4,315,028 describes a method of treatment of arthritis employing substituted cysteines.

The S-methyl derivative of methionine, S-methyl methionine, also known as vitamin U has been shown to have benefit as an anti-ulcer compound and to have benefit for allergies. The same benefit is shown for carboxyl esters and N-acyl derivatives (Kowa, DT 282-704). However, in this teaching no distinction is made for the d- and l- isomers of S-methyl methionine or its derivatives and no claim is made that these compounds act through anti-inflammatory mechanisms.

The patent to Damico, U.S. Pat. No. 3,952,115 describes foodstuffs containing N-acyl l-methionine esters and N-acyl l-cysteine esters. d-Isomers are specifically excluded because they are "not nutritionally available".

The patent to Fahim, U.S. Pat. No. 4,711,780, shows the benefit of the combination of cysteine with vitamin C and zinc salts in a topical mixture for stimulating cell proliferation. The benefit of methionine is claimed but not shown. No demonstration of benefit or claim for systemic administration is made.

The patent to Bayless, U.S. Pat. No. 4,902,718, describes the use of methionine compounds for respiratory. The patent to Bayless, U.S. Pat. No. 4,927,850, describes the use of methionine compounds for calcium normalization, hypertension and osteoporosis. The patent the Hirsch, U.S. Pat. No. 5,053,429 describes the use of methionine compounds for inflammatory pain. The patent to Hirsch, U.S. Pat. No. 5,084,482, describes the benefits of methionine compounds for ischemic thrombotic and cholesterolemic diseases. These patents also teach the use of glycine and serine alone or in addition with vitamins and minerals to reduce the side effects which are associated with elevated homocysteine resulting from methionine consumption.

From the extensive infection of humans with HIV and the impending epidemic of AIDS there is an immediate need for improved and safe means of treating disease conditions and delaying the onset of symptoms of AIDS.

It is an object of the invention to provide methods for the treatment of disease conditions and delay the onset of symptoms which occur in AIDS.

It is also an object of the invention to provide means prevent or alleviate elevation of serum triglycerides that may result from excess methionine intake.

It is also an object of the invention to provide a safe means of thiol repletion.

These and other objects, features and advantages will be seen from the following detailed description of the invention.

SUMMARY OF THE INVENTION

Our invention is based on the discovery that certain methionine or methionine-type compounds in the dl-form at relatively high, well-tolerated doses are potent antioxidant and antiinflammatory agents in man which are of benefit to persons infected with the Human Immunodeficiency Virus (HIV). The compounds are especially important when administered or used for treatment in dosage form, for relieving, inhibiting or abolishing any of various inflammatory disease conditions or syndromes presenting as thiol depletion, which include HIV infection. The methionine compounds in high daily dosage according to the invention thus may act in vivo to inhibit oxidative effects on sulfhydrals such as the action of hypochlorous acid to reduce proteolysis and tissue damage.

Novel methods and compositions for the prevention and treatment of disease conditions of man may be attributable to or result from nutritional deficiency of the l-form of methionine, such as glutathione depletion, are also disclosed.

Novel methods and compositions for the prevention of side-effects due to chronic administration of low doses of methionine in man by inclusion of glycine or serine for the normalization of serum triglyceride levels are disclosed.

For purposes of the invention, one uses at least one methionine-type compound selected from the methionine hydroxy analogs and methionine compounds having the structural formula I

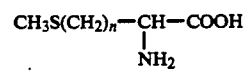

l-, dl or d form and pharmaceutically acceptable N-(mono- and di- carboxylic acid) acyl derivatives and alkyl esters thereof, where n is an integer from 1 to 3.

Thus, the methionine-type compound (for convenience some times referred to herein as "methionine" or "methionine compound") may be normethionine (n=1), methionine (n=2), homomethionine (n=3), the hydroxy analog, or the acyl or alkyl ester derivatives thereof, as defined. Exemplary acyl derivatives are the formyl, acetyl, propionyl, and succinyl derivatives, of which the formamide, acetamide and succinyl derivatives are preferred. Exemplary ester derivatives are methyl, ethyl and isopropyl esters.

The mechanism underlying the present invention is believed to be that the methionine compound acts in vivo to reduce the effect of release by polymorphonuclear leukocytes (PMNs) of hypochlorous acid and other oxidants so that systemic oxidation especially of sulfhydrals, proteolysis, and tissue damage are inhibited. It is believed that the l-form of the methionine compound serves to fulfill its essential, recognized nutritional need that results especially in the presence of serine or glycine to provide precursors for glutathione and other antioxidants whereas it is the d-form that has a different action at high dosage which is a well tolerated antioxidant and antiinflammatory activity.

To the extent that conditions benefiteed by the consumption of dl-methionine are the result of a dietary deficiency of l-methionine it may be desirable to replenish methionine in food products as is currently done for a number of vitamins that are also made unavailable by food processing. The invention also employs methods and compositions for providing methionine in the final product for consumption in the amount that provides for replacement of unavailable methionine an additional methionine that would accomplish the teachings herein where it is desirable to obtain the additional antioxidant amount in a normal food item. To safely provide low levels of additional dietary methionine it is necessary according to the invention to include additional glycine or serine in order to prevent the elevation of serum triglycerides which occur at relatively low doses of methionine.

Damico (U.S. Pat. No. 3,952,115) teaches the addition of N-acyl l-methionine as a preferred method to reduced undesired odor effects of methionine supplementation. He teaches that the amount of methionine to be added to methionine-deficient protein can be determined by amino acid analysis in the case of proteins known to below in methionine content such that methionine should be added up to the level characteristic for egg protein (an amount recognized by the U.S. Food and Drug administration as the upper limit for addition of methionine for commercial foods). In the case of proteins for which methionine is lost by food processing such as extracted protein of soy bean he teaches that the amount of methionine to be added for proper nutrition involves adding methionine derivatives as determined by rodent feeding experiments.

Because of the role that inflammatory cells play in long term tissue damage and because of the known dietary correlations of several serious inflammatory pain conditions that may be affected by reduced control of inflammatory cells, correction of a chronic marginal dietary deficiency of methionine and thus improved long term control of inflammatory cells can be expected to reduce the severity or incidence of these conditions. As an example of the possible contribution of reduced control of inflammatory cells. especially PMNs, that may be due to a marginal dietary deficiency of available methionine, it had been shown that produces of stimulated PMNs can cause cellular transformation characteristic that has been associated with carcinogenesis (Weitzman, et. al., Science, 227:1231-3, 1985). Smokers that have been exposed to asbestos have very much higher lung cancer rates than exposed non-smokers, and it has been shown that smoking oxidizes a methionine residue in alpha-1-protease inhibitor, thus allowing increased lung proteolysis. Other examples of damage due to reduced control of PMNs include arthritis and lung inflammation.

DESCRIPTION OF PREFERRED EMBODIMENTS

The best method to practice the teachings of described compounds depends on the particular conditions being treated and the compositions that are required to produce optimal results. plycine and serine are needed to prevent abnormal triglyceride levels which otherwise would occur when compounds containing l-methionine or its derivatives are consumed.

In addition, in those cases where deficiencies of other dietary antioxidants may limit the total benefit to be derived from methionine compounds they should be provided with the methionine compounds. When methionine compounds are used in the upper portion of the dosage range dissolution of the compound in the stomach should be slowed. Also, individuals that are more sensitive to gastric upset should be provided with slow dissolving compositions to get effective relief.

For this purpose, the methionine compound and other antioxidants are present in an appropriate pharmaceutical dosage form, preferably in a sustained release or controlled release form (e.g. an enteric coated or slow release form, which may be per se conventional), to enhance or ensure release in the intestine rather than the stomach, optionally with suitable excipients, such that each substance contributes its respective anti-inflammatory effect when a unit dosage of the composition is administered. A preferred composition for human use is one where the unit dosage of the methionine compound, preferably dl- methionine, is sufficient to provide a total daily dosage range of about 1.0 to 10 gm/70 kg of body weight.

In another preferred aspect, the method employs a therapeutic antiinflammatory composition in unit dosage form comprising an antiinflammatory effective amount of at least on methionine compound as defined above, and at least one member from the groups (a) through (e); (a) a triglyceride normalizing amount of glycine or serine as defined below, (b) at least one homocysteine affecting vitamin as defined above, in an amount sufficient to enable the systemic conversion, when consumed or administered, of homocysteine to methionine or cysteine, (c) at least one dietary antioxidant in a synernistically antioxidant effective amount selected from a group of dietary antioxidants, (d) an inactive excipient that provides insolubility in the stomach and solubility in the intestines; and (e) combinations thereof. Preferred dietary antioxidants are vitamins A, C, E, selenium, or zinc, each preferably in a total daily dosage range of: vitamin A, 500 to 50,000 I.U.; vitamin C, 1 to 1,000 mg; vitamin E, 1 to 150 I.U.; selenium, 1 to 200mcg; zinc, 1 to 50 mg; and combinations thereof. Since the antioxidant characteristics, metabolism, and mechanism of methionine compounds differ from those of other antioxidants, a synergistic antiinflammatory effect can be expected.

The benefit of glycine and serine especially, and vitamin B6 inference, for the adult male subject typically depends on their effect in reducing elevated triglycerides. Yanagita shows that in rats, 0.3% added l-methionine to the diet causes a more than three-fold increase in liver triglycerides (Yanagita, et. al., Agric. Biol. Chem, 48:815-6, 1984). Methionine and cysteine, the two amino acids which contain sulfur, constitute 3% of all the amino acid of proteins. Thus on a diet as low as 10% protein the addition of 0.3% represents only a doubling of dietary sulfur amino acids. Sugiyama, et. al., (Agric. Biol. Chem., 49: 3455-61, 1985) showed that the addition of 2.5% glycine to a methionine supplemented rat diet had no effect on plasma triglyceride levels. Thus the triglyceride lowering effect in humans of glycine when added to methionine is contrary to expectation. Betaine, while effective for lowering homocysteine was not effective for reducing triglycerides, other unexpected result. Elevated triglycerides are undesirable because they ar associated with increased incidence of gallstones (In: Epidemiology and Prevention of Gallstone Disease, L. Capocaccia, et al, eds., 1984, MTP Press, Ltd., Lancaster, p. 77-84). The benefit for reducing triglycerides is shown in the following human blood values:

| | |
|---|---|
| Normal range for triglycerides | 45-150 mg/dl |
| Consumption of dl-methionine, 1.5 gm/day (0.5 gm, 3 times per day) plus 1.0 gm/day betaine (0.5 gm 2 times/day) | 224 mg/dl |
| Consumption of dl-methionine, 1.5 gm/day (0.5 gm, 3 times per day) plus 1.5 gm/day glycine (0.5 gms 3 times/day) | 129 mg/dl |

These results show that glycine but not betaine was effective in allowing normal blood values for triglycerides during daily consumption of methionine by a human subject.

In another preferred aspect, the invention concerns a method for treating thiol depletion in a subject. The method comprises administering to a subject a composition in dosage form containing an effective thiol raising amount of at least one methionine compound with glycine or serine. Preferably for this purpose, the methionine is administered in a total daily dosage range of about 1 to 10 gm/70 kg of body weight and is continued daily until the thiol levels are normalized. In a preferred embodiment, the dl-form of methionine is used with glycine and serine, preferably in a daily oral dose of 2.0 grams taken 2 times in spaced equal doses with 1.0 gram of glycine and serine taken at 2 spaced equal doses. In another preferred embodiment selenium is taken with the methionine and glycine or serine in a total daily dose of about 2 to 200 micrograms.

In another preferred aspect, the invention concerns a therapeutic antiinflammatory composition in unit dosage form comprising an antiinflammatory effective amount of at least one methionine compound as defined above, and a triglyceride normalizing amount of glycine or serine as defined above in Lipid Normalization.

In another preferred aspect, the method employs a therapeutic composition in unit dosage form for treating thiol depletion in a subject comprising a thiol increasing amount of the l-form of methionine and a thiol sparing amount of the d-form of methionine, as defined above, and a triglyceride normalizing amount of glycine or serine as defined below, and at least one member from the groups (a) and (b); (a) at least one homocysteine affecting vitamin as defined above, in an amount sufficient to enable the systemic conversion, when consumed or administered, of homocysteine to methionine or cysteine, (b) an inactive excipient that provides insolubility in the stomach and solubility in the intestines: and (c) combinations thereof.

An example of the thiol repletion benefit of dl-methionine and glycine is shown for a HIV-positive subject with AIDS associated disease conditions. The patient had increased sedimentation rate for red blood cells, leukoplakia (monilia) and had been losing weight over a 7 month period prior to treatment with dl-methionine, 1 gram twice a day, glycine, 0.5 gm twice a day, folate, 1 mg per day and one multivitamin. After 2 months treatment weight loss had been arrested (gained 3 lbs.), the leukoplakia (thrush) had resolved and the red cell sedimentation rate dropped to 41 from a high of 105. Based on the antioxidant and metabolic properties of dl-methionine and on the reduced blood levels of glutathione in symptom-free HIV-positive subjects the methionine-glycine benefit seen in the example above is thought to be moderated by thiol repletion.

Detailed methods for the preparation and tableting of methionine compounds are contained in U.S. Pat Nos. 4,902,718, 4,927,850, 5,053,429, and 5,084,482, which methods are incorporated herein by reference.

Having thus described our invention, what we claim and desire by Letters Patent to secure are the following:

1. A method for ameliorating the inflammatory symptoms of human immunodeficiency virus infection and AIDS in man employing the administration to the subject in need thereof a therapeutic composition in dosage form consisting essentially of an anti-inflammatory amount of methionine compound selected from the group consisting of dl-methionine, methyl, ethyl, propyl and isopropyl esters thereof, N-acetyl-dl-methionine, N-formyl dl-methionine and methyl, ethyl, propyl and isopropyl esters of N-acetyl and N-formly dl-methionine to provide a total daily methionine dosage in the range of 1.0 to 10 grams per 70 kg of body weight and further comprising at least one triglyceride normalizing compound selected from the group consisting of serine and glycine, the serine and glycine are present from 1/5 to 3 times the methionine compound present.

* * * * *